United States Patent [19]
Brown et al.

[11] Patent Number: 6,015,377
[45] Date of Patent: Jan. 18, 2000

[54] MAGNETIC PENETRATOR

[75] Inventors: L. Edward Brown, Cambridge; Adam R. Resch, Kitchener, both of Canada

[73] Assignee: 1184949 Ontario Inc., Cambridge, Canada

[21] Appl. No.: 09/086,607

[22] Filed: May 29, 1998

[51] Int. Cl.[7] .................................................. A61N 2/00
[52] U.S. Cl. .................................................................. 600/9
[58] Field of Search ............................................. 600/9–15

[56] References Cited

U.S. PATENT DOCUMENTS

| | | | |
|---|---|---|---|
| 645,433 | 3/1900 | Strange et al. ........................... | 600/15 |
| 5,295,494 | 3/1994 | Rodriguez .............................. | 600/9 X |
| 5,667,469 | 9/1997 | Zhang et al. ............................. | 600/9 |
| 5,707,333 | 1/1998 | Bakst ..................................... | 600/9 |

*Primary Examiner*—Samuel Gilbert
*Attorney, Agent, or Firm*—Dimock Stratton Clarizio; Mark B. Eisen

[57] ABSTRACT

The invention provides a device having a plurality of magnets, preferably mounted at an angle relative to one another, with their south poles oriented toward a magnetic backing plate. The north poles of the magnets direct negative magnetic energy forwardly to create a magnetic field able to penetrate deeply into bodily tissue.

20 Claims, 4 Drawing Sheets

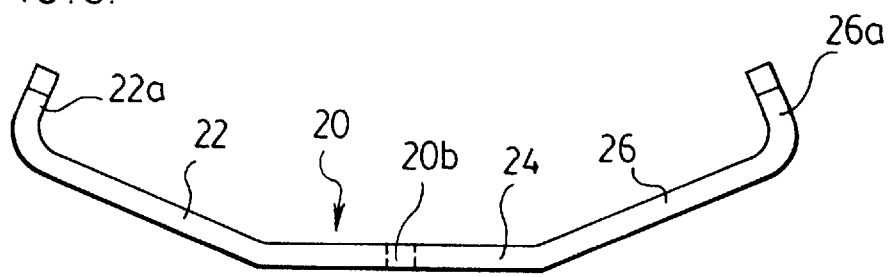
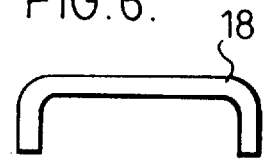
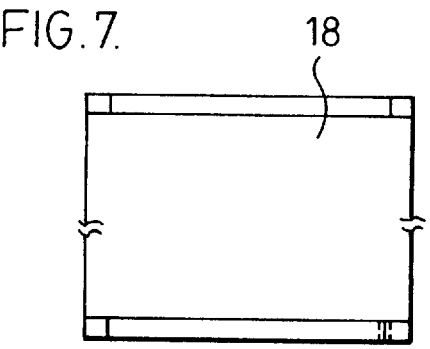
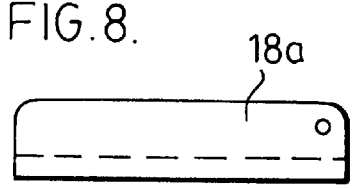
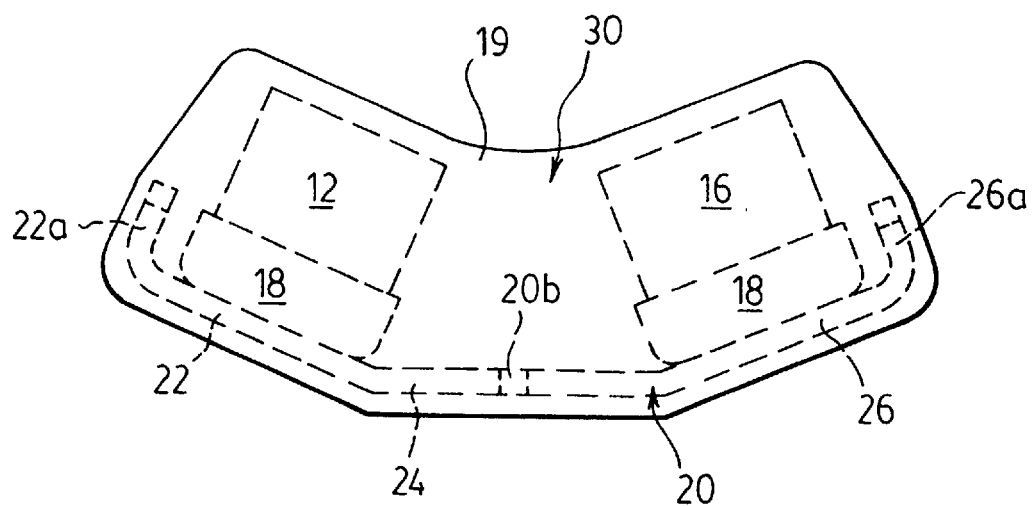

MAGNETIC PENETRATOR

FIELD OF THE INVENTION

This invention relates to magnetic health aids. In particular, this invention relates to a magnetic health aid for pain management and wellness of the body that contributes to the wellness of bodily tissues, including cells, muscle, bones, organs and blood, by exposing the body to magnetic fields which energize the molecules of the body at the cellular level.

BACKGROUND OF THE INVENTION

The use of magnetic fields to contribute to wellness of the body has been in practice for centuries around the world. Currently used primarily in Europe and Eastern Hemisphere countries, the use of magnetic fields was also common in North America until the introduction of modern drugs for treatment of pain and infection.

Magnetic energy is known to be useful in the treatment of fluids flowing through a conduit. One of the beneficial effects of magnetic treatment of a fluid is that particles in the fluid stay more finely dissolved. For example, in the case of water flowing through a magnetic field calcium suspended in the water will not form a scale and degrade the system.

Magnetic energy works at the atomic level. When a magnetic field is not present, the energy levels of atoms in a system decrease and crystallization occurs more readily. Magnetism is one form of energy that is capable of penetrating most substances and affecting atoms within it directly.

Hydrogen, the primary building block of all matter and of which 63 percent of the body's atoms is comprised, is the atom, because of its makeup, most susceptible to being affected by magnetic energy. When the correct magnetic field interacts with a hydrogen atom, it alters the energy level of the atom and increases the efficiency of hydrogen-based processes, enhancing hydration and hydrolysis.

All life evolved in the Earth's magnetic field and all chemical reactions, both within and outside of the body, are designed to use that magnetic field. When any system receives less magnetic energy than it requires, functions slow down and become inefficient. This is why calcium-laden water, when shielded from the the Earth's magnetic field or when the Earth's magnetic field is disrupted, drops the calcium out of the solution and forms hard calcite crystals.

Similarly, when magnetic energy is applied to body tissues, it works at the cellular level to energize atoms. Nutrients and elements in the blood stay more finely dissolved and are thus more bio-available to bodily cells and tissues. Nutrients are delivered to the cell more efficiently and bodily wastes and toxins are more efficiently carried away and flushed by the body's filtering systems.

When deprived of the Earth's magnetic energy, nutrients in body fluids lose energy and form crystals, such as plaque, calcium deposits, uric acid crystals and others. These crystallized nutrients are no longer available to the body cells.

Because humans evolved in the Earth's magnetic field, the human body functions less efficiently when receiving less magnetism than it was designed to use. Most people currently receive less magnetic energy than they need for two reasons: the Earth's magnetic field is one-tenth as strong as it was several thousand years ago, and modern lifestyles surround people with steel and iron structures that absorb much or all of the magnetic field that would normally penetrate the body.

Applying the proper magnetic fields to bodily tissues adds needed energy, which results in the crystallized nutrients and elements being redissolved and made available to cells in the body.

Applications of properly designed magnetic fields to the body has proven to allay the pain and other symptoms associated with many ailments, including asthma, back pain, burns, chronic fatigue syndrome, cataracts, fibromyalgia, arthritis, blood pressure and circulation, migraines, muscles strains, joint problems and others.

In addition, magnetic energy applied to the body promotes faster healing, general wellness and increased vitality, due to the improved use of nutrients by bodily tissues.

SUMMARY OF THE INVENTION

The invention provides a concentration of magnetic energy in a focussed field specifically designed to penetrate deeply into bodily tissues, in order to maximize the delivery of magnetic energy to the body generally or to specific areas of the body that need it most. The invention focuses the magnetic field in such a way as to maximize effects on the area to which it is applied, providing beneficial effects in an efficient manner. Thus, pain relief and alleviation of symptoms may occur more rapidly using the invention as opposed to a less focused bio-magnetic device.

The invention accomplishes this by providing a plurality of magnets mounted in spaced relation and having their south poles oriented toward a magnetic backing plate and their north poles directed forwardly so that when applied to the body the negative magnetic energy is concentrated in a focussed field that penetrates deeply into bodily tissues. In a preferred embodiment at least two magnets are mounted at an angle relative to each other, and the device is encased in a non-magnetic material.

The present invention thus provides a device for creating a penetrating magnetic field, comprising a plurality of magnets mounted in spaced relation and having south poles oriented toward a magnetic backing plate and north poles oriented in a forward direction to direct negative magnetic energy forwardly from the backing plate. In a further aspect of the invention the device is encased in a non-magnetic material. In a still further aspect of the invention at least two magnets are mounted at an angle relative to each other.

BRIEF DESCRIPTION OF THE DRAWINGS

In drawings which illustrate by way of example only a preferred embodiment of the invention, FIG. 5 is a a top plan view of the backing plate for the magnetic assembly of FIG. 4, FIG. 6 is a cross-section of a magnet holder in the magnetic assembly of FIG. 4, FIG. 7 is a front elevation of the magnet holder of FIG. 6, FIG. 8 is a bottom plan view of the magnet holder of FIG. 6, FIG. 9 is a top plan view of a preferred embodiment of the invention with two magnets.

DETAILED DESCRIPTION OF THE INVENTION

Figure 1:
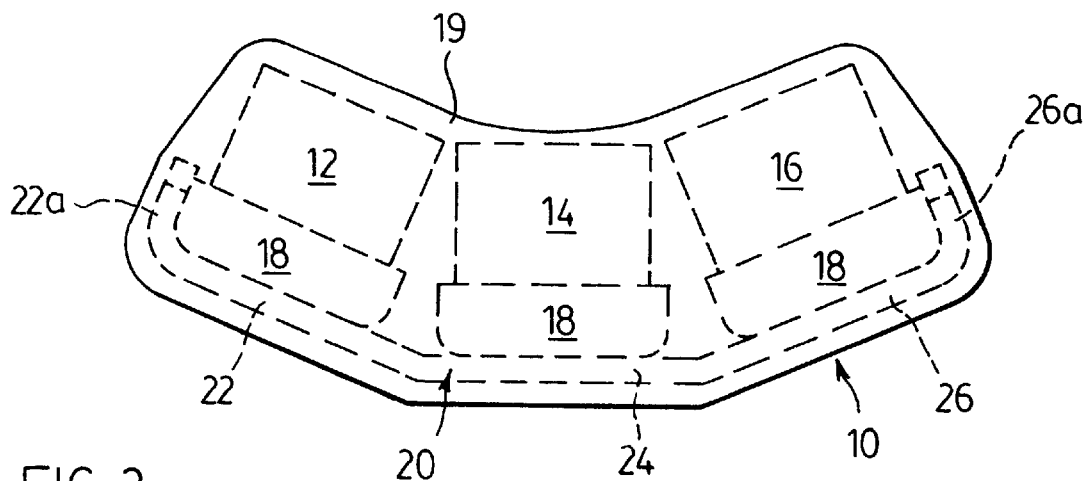
FIG. 1 is a top plan view of a preferred embodiment of the invention with three magnets.
Figure 2:
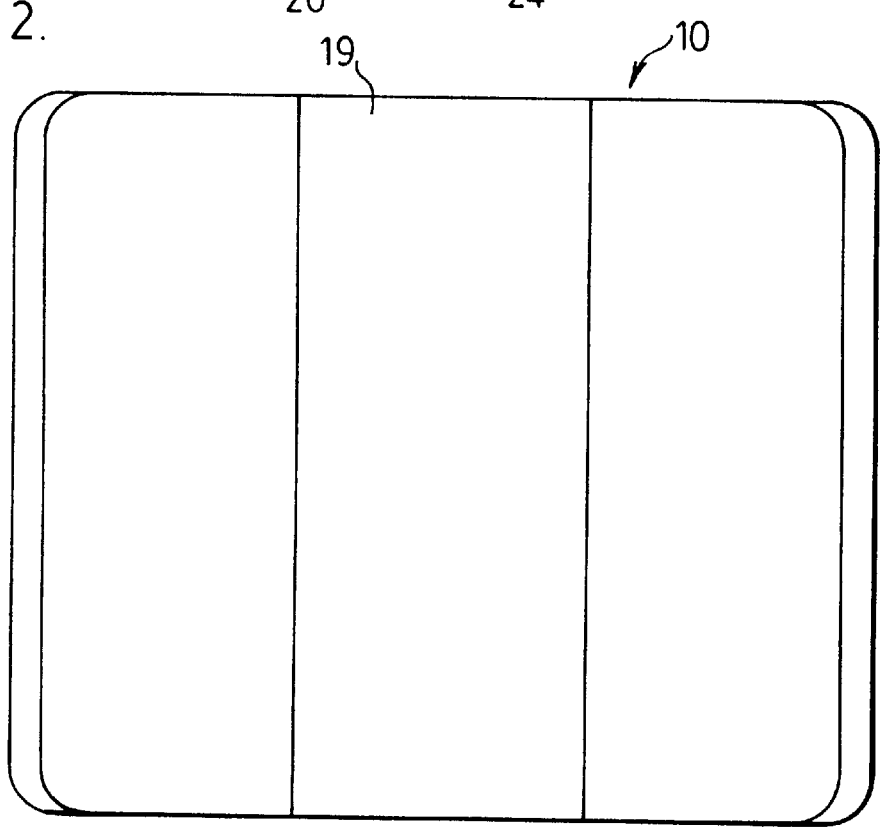
FIG. 2 is a front elevation of the embodiment of FIG. 1.
Figure 3:
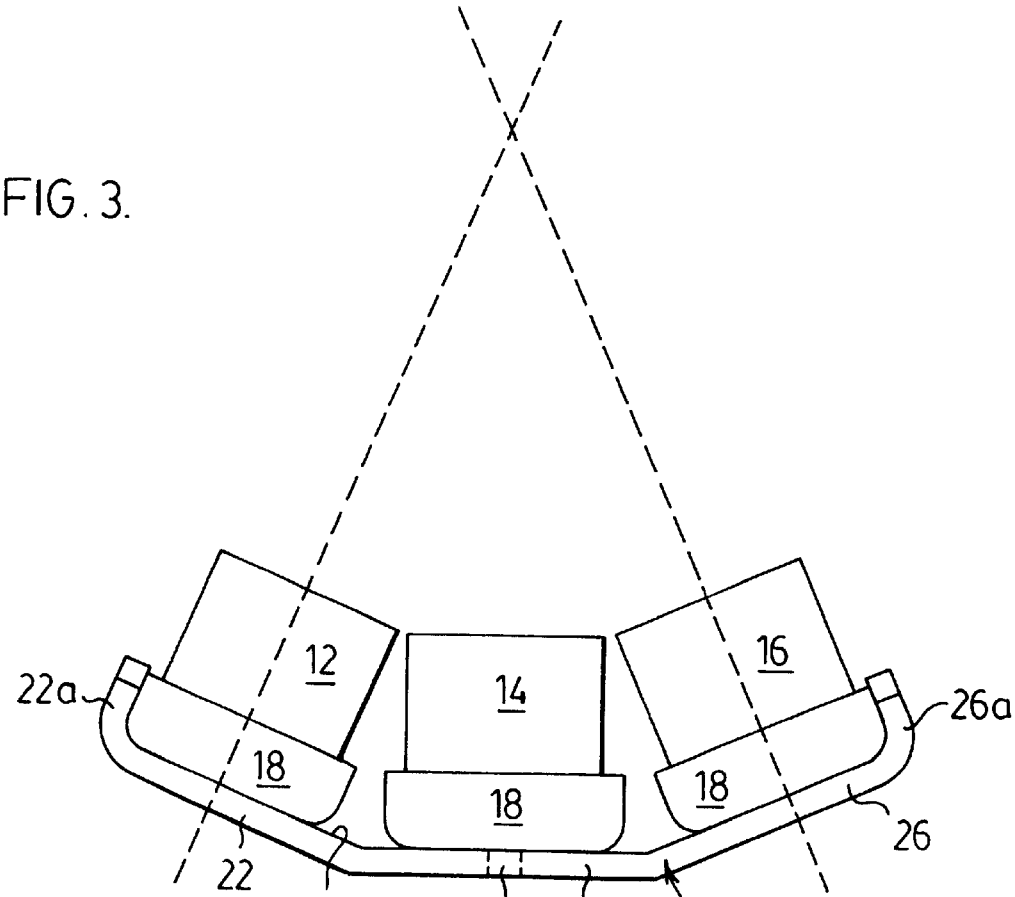
FIG. 3 is a a top plan view of the magnetic assembly in the embodiment of FIG. 1.
Figure 4:
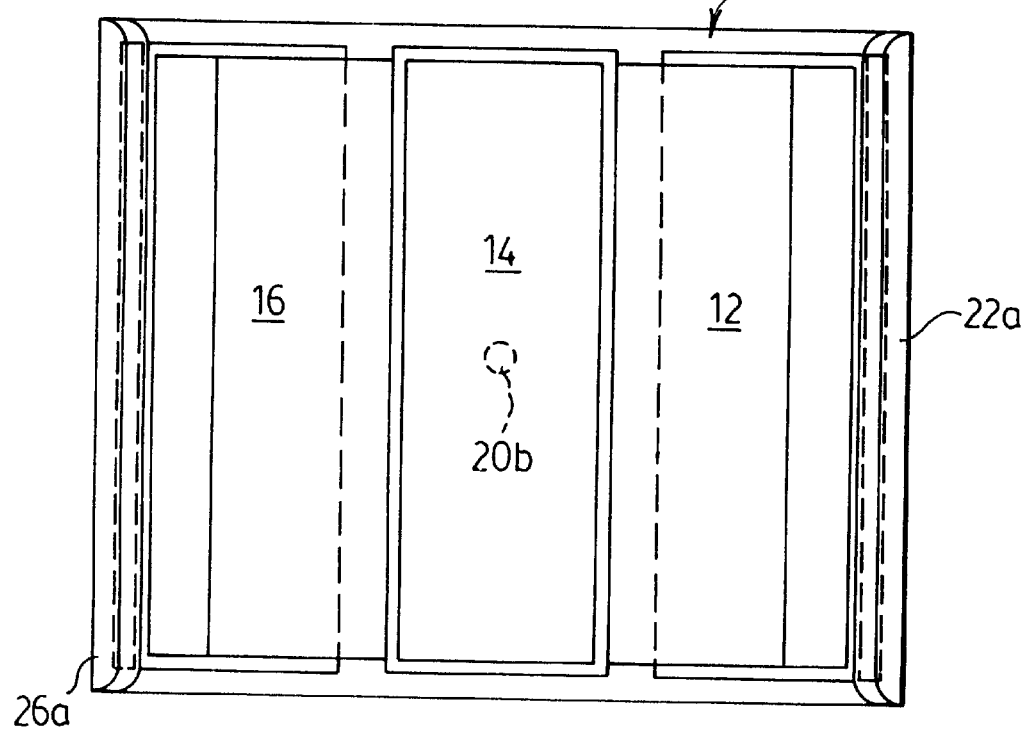
FIG. 4 is a a front elevation of the magnetic assembly in the embodiment of FIG. 1.

A first preferred embodiment of the magnetic penetrator device 10 of the invention is illustrated in FIGS. 1 and 2. The device 10 includes a magnetic assembly, illustrated in FIG. 3, comprising a plurality of permanent magnets 12, 14, 16, the size and strength of each magnet being selected according to the level of penetration and amount of magnetic energy desired to be supplied to the tissue to be treated.

The magnets 12, 14, 16 are disposed along the front surface 20a of a backing plate 20, illustrated in FIG. 5, preferably composed of 12 gauge mild steel or another ferrous material. The magnets 12, 14, 16 are mounted in spaced relation, preferably evenly spaced apart, in magnet holders 18, also composed of 12 gauge mild steel or another ferrous material, which are preferably "C" shaped in cross-section as shown in FIGS. 6 to 8 and include end plates 18a. The magnet holders 18 may be affixed to the backing plate 20 by a silicone-based adhesive compound or other similar adhesive material that does not react with steel, and the magnets 12 are likewise affixed to the magnet holders 18.

The entire magnetic assembly is preferably encased in a non-magnetic material which is preferably a rugged, durable thermoplastic or urethane compound 19. The backing plate 20 may include a hole 20b through the centre portion 24 for purposes of mounting the magnetic assembly for molding. The plastic 19 reinforces the backing plate 20, protects the components of the device 10 and the components are embedded in the plastic 19 which maintains all of the components of the device 10 in their proper physical relationship. The plastic casing 19 is also hygienic for use and easily cleaned.

The magnets 12, 14, 16 are each oriented with their south poles directed rearwardly, toward the backing plate 20. The north poles of the magnets 12, 14, 16 face forwardly and direct negative magnetic energy forwardly from the front surface 20a of the backing plate 20 through a magnetic field region between the magnets 12, 14, 16.

As shown in FIG. 5, in the preferred embodiment the backing plate 20 comprises a straight centre portion 24 with wings 22, 26 extending symmetrically from the centre portion 24 at an angle. The wings 22, 26 may terminate in flanges 22a, 26a generally orthogonal to the wings 22, 26, to assist in aligning the magnet holders 18 for mounting. The magnet holders 18 should be spaced so that the magnets 12, 14, 16 do not touch each other.

In use the device 10 is placed over an area of the body to be treated, and held or strapped in position with the north poles of the magnets 12, 14, 16 directed forwardly toward the body tissue. Optimally the angle between the centre portion and each wing is approximately 157.5°, so that when mounted the axes of the outer magnets 12, 16, shown in phantom lines in FIG. 3, intersect at an angle of approximately 45°; however, the device 10 may still be effective within some deviation about the optimal angle. The negative magnetic energy is directed forwardly from the front surface 20a of the backing plate 20 and concentrated in a focussed field that penetrates deeply into bodily tissues, to maximize the delivery of magnetic energy to the body generally or to specific areas of the body.

Figure 10:
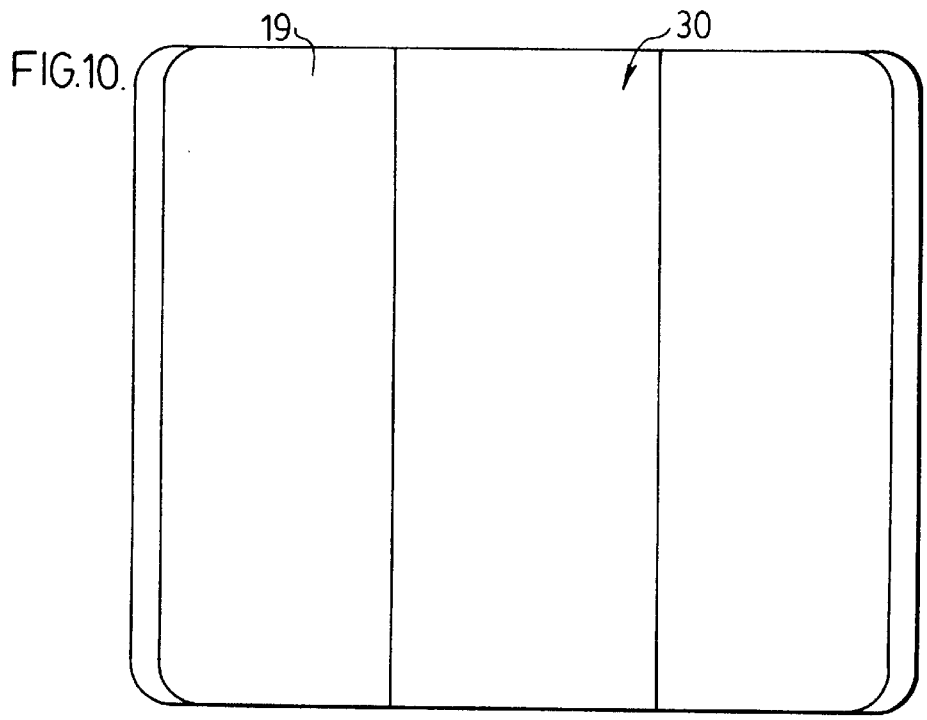
FIG. 10 is a front elevation of the embodiment of FIG. 8.
Figure 11:
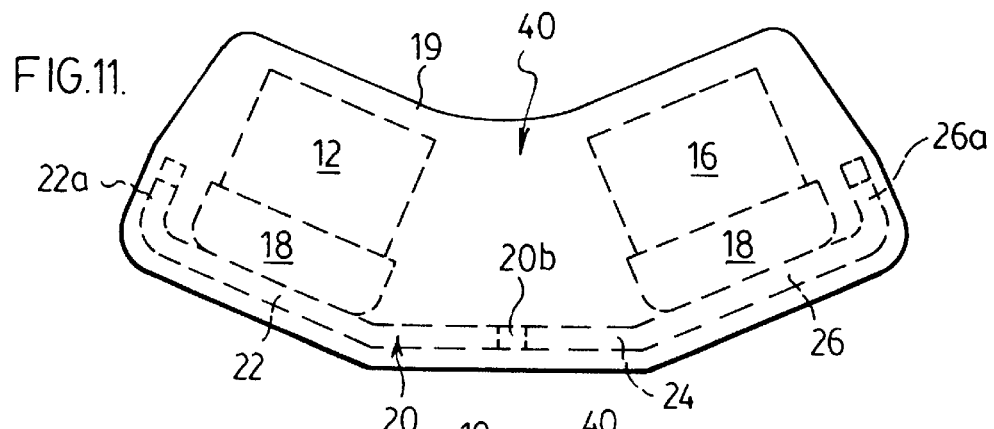
FIG. 11 is a top plan view of a further preferred embodiment of the invention with two magnets.
Figure 12:
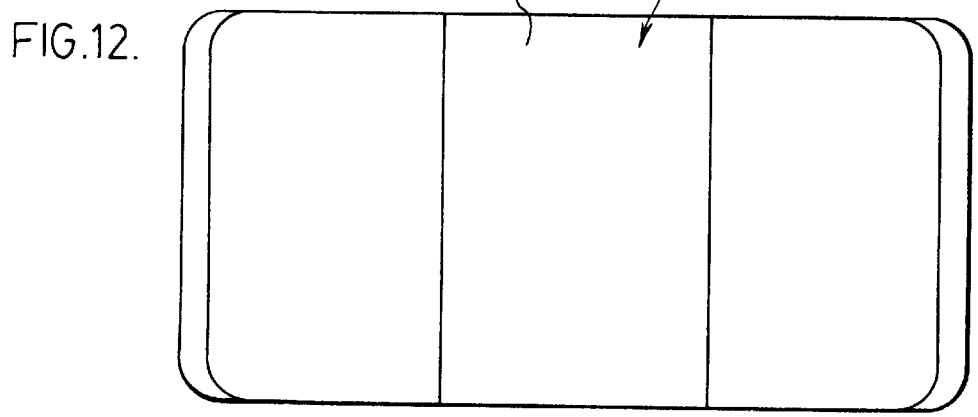
FIG. 12 is a front elevation of the embodiment of FIG. 10.

In a further embodiment illustrated in FIGS. 9 and 10 the device 30 is configured as described above, but includes only the two outer magnets 12, 16 mounted on the wings 22, 26. This embodiment is more compact since the magnets 12, 16 can be mounted closer together than in the device 10 of the above-described embodiment. Because the magnets 12, 16 are more closely spaced in the device 30 the focus of the magnetic field is closer to the device 30 for shallower penetration. The construction and operation of the device 30 is otherwise as described above. An even more compact embodiment is illustrated in FIGS. 11 and 12, illustrating a device 40 which is identical to the device 30 but shorter, as can be seen in FIG. 12.

The invention having been thus described by way of example only, it will be apparent to those skilled in the art that certain modifications and adaptations may be made without departing from the scope of invention. For example, without limiting the foregoing, more or fewer magnets may be suitable for any particular application, and the sizes of the magnets can be selected as desired. The invention is intended to include all such modifications and adaptations as fall within the scope of the appended claims.

We claim:

1. A device for creating a penetrating magnetic field, comprising a plurality of magnets mounted in spaced relation and having south poles oriented toward a substantially rigid magnetic backing plate and north poles oriented in a forward direction to direct negative magnetic energy forwardly from the backing plate, whereby the magnets are retained in a predetermined angular relation relative to each other.

2. The device of claim 1 in which the device is encased in a non-magnetic material .

3. The device of claim 2 in which the non-magnetic material is a thermoplastic.

4. The device of claim 1 in which at least two magnets are mounted at an angle relative to each other of approximately 157.5°.

5. The device of claim 4, in which two magnets are mounted on wings of the backing plate, the wings being oriented at an angle relative to each other.

6. The device of claim 5, in which the wings extend from a center portion of the backing plate.

7. The device of claim 6, in which the wings are provided with generally orthogonal outer flanges.

8. The device of claim 6, in which a magnet is mounted on the center portion.

9. The device of claim 5, in which the angle between the axes of the magnets is approximately 45°.

10. The device of claim 4, having two magnets.

11. The device of claim 4, having three magnets.

12. The device of claim 1 in which the magnets are mounted to magnetic magnet holders which are mounted to the backing plate.

13. The device of claim 12, in which the magnets are mounted by a silicone or similar adhesive compound.

14. The device of claim 12, in which the magnet holders are "C" shaped in cross-section.

15. The device of claim 1 in which the backing plate is formed from steel.

16. A device for creating a penetrating magnetic field, comprising a plurality of magnets mounted in spaced relation and having south poles oriented toward a substantially rigid magnetic backing plate and north poles oriented in a forward direction, the device being encased in a non-magnetic material, whereby the magnets are retained in a predetermined angular relation relative to each other and wherein negative magnetic energy is directed forwardly from the backing plate through the non-magnetic material.

17. The device of claim 16 in which two magnets are mounted on wings of the backing plate, the wings being oriented at an angle relative to each other.

18. The device of claim 17 in which the wings extend from a centre portion of the backing plate.

19. The device of claim 18 in which the wings are provided with generally orthogonal outer flanges.

20. The device of claim 18 in which a magnet is mounted on the centre portion.

* * * * *